United States Patent
Ikezawa et al.

(10) Patent No.: US 12,042,427 B2
(45) Date of Patent: Jul. 23, 2024

(54) TEMPERATURE CONTROL AGENT, AND HEAT-GENERATING COMPOSITION AND WARMING DEVICE EACH USING SAME

(71) Applicant: FERRIC INC., Tokyo (JP)

(72) Inventors: Masayoshi Ikezawa, Tokyo (JP); Yuuki Okamura, Tokyo (JP); Hirokazu Miyashita, Tokyo (JP); Eiji Miyashita, Tokyo (JP)

(73) Assignee: FERRIC INC., Tokyo (JP)

( * ) Notice: Subject to any disclaimer, the term of this patent is extended or adjusted under 35 U.S.C. 154(b) by 963 days.

(21) Appl. No.: 15/733,400

(22) PCT Filed: Feb. 1, 2019

(86) PCT No.: PCT/JP2019/003587
§ 371 (c)(1),
(2) Date: Jul. 21, 2020

(87) PCT Pub. No.: WO2019/151472
PCT Pub. Date: Aug. 8, 2019

(65) Prior Publication Data
US 2020/0360179 A1    Nov. 19, 2020

(30) Foreign Application Priority Data

Feb. 5, 2018  (JP) .................................. 2018-018047

(51) Int. Cl.
*A61F 7/03*       (2006.01)
*A61H 39/06*   (2006.01)
*C09K 5/18*     (2006.01)

(52) U.S. Cl.
CPC .................. *A61F 7/034* (2013.01); *C09K 5/18* (2013.01)

(58) Field of Classification Search
CPC ............. A61H 39/06; A61F 2007/0047; A61F 2007/0244; A61F 2007/026;
(Continued)

(56) References Cited

U.S. PATENT DOCUMENTS 6,336,935 B1    1/2002 Davis et al.
9,668,913 B2    6/2017 Matsuo
(Continued)

FOREIGN PATENT DOCUMENTS

CN    103387737    11/2013
CN    103920092     7/2014
(Continued)

OTHER PUBLICATIONS

Temperature Control Agent, and Heating Composition, Miyashita et at., 2016 (English Translation of WO document).*
(Continued)

*Primary Examiner* — Tigist S Demie
(74) *Attorney, Agent, or Firm* — Grüneberg and Myers PLLC

(57) ABSTRACT

A means can be used instead of or with conventional temperature control to achieve warming device temperature control at a lower cost, prevent or reduce deterioration of a warming device over time, and lower generated heat temperature due to storage at high temperatures. The warming device can be used for the same. A higher level temperature control means can be used for warming devices for medical applications. An improved warming device can be used for medical applications with a high level of safety and efficacy. A temperature control agent controls a maximum temperature of a warming device with a heat generating composition that generates heat by reaction with oxygen. Said agent includes an aliphatic compound that has a particle form that will not pass through a standard sieve with a #60 mesh, a (Continued)

melting point of 35-65° C., and an aqueous solubility (g/100 mL) at 20° C. of ≤5.

16 Claims, 7 Drawing Sheets

(58) Field of Classification Search
CPC ........ A61F 2007/0292; A61F 2007/038; A61F 7/03; A61F 7/032; A61F 7/034; A61F 2007/022
See application file for complete search history.

(56) References Cited

U.S. PATENT DOCUMENTS

| | | | |
|---|---|---|---|
| 9,671,133 | B2 | 6/2017 | Sonoda et al. |
| 2003/0008578 | A1 | 1/2003 | Brooks |
| 2004/0217325 | A1 | 11/2004 | Usui et al. |
| 2008/0141437 | A1 | 6/2008 | Braunecker et al. |
| 2011/0190714 | A1 | 8/2011 | Oda et al. |
| 2013/0008425 | A1* | 1/2013 | Matsuo ................ A61F 7/034 126/204 |
| 2013/0345649 | A1 | 12/2013 | Stockley, III et al. |
| 2014/0109891 | A1 | 4/2014 | Sonoda et al. |
| 2017/0239085 | A1 | 8/2017 | Miyashita et al. |

FOREIGN PATENT DOCUMENTS

| | | |
|---|---|---|
| JP | 58-11581 | 1/1983 |
| JP | 2001-89757 | 4/2001 |
| JP | 2001-170099 | 6/2001 |
| JP | 2002-60741 | 2/2002 |
| JP | 2004-65949 | 3/2004 |
| JP | 2006-247233 | 9/2006 |
| JP | 2008-214535 | 9/2008 |
| JP | 2011-212170 | 10/2011 |
| JP | 4981960 | 7/2012 |
| JP | 5073035 | 11/2012 |
| JP | 2013-9747 | 1/2013 |
| JP | 2013-183932 | 9/2013 |
| WO | 99/00078 | 1/1999 |
| WO | 03/097764 | 11/2003 |
| WO | 2016/063815 | 4/2016 |
| WO | WO-2016063815 A1 * | 4/2016 ............... A61F 7/03 |

OTHER PUBLICATIONS

International Search Report issued Mar. 26, 2019 in PCT/JP2019/003587 with English translation, 5 pages.
Written Opinion issued Mar. 26, 2019 in PCT/JP2019/003587.
English translation of Written Opinion issued Mar. 26, 2019 in PCT/JP2019/003587.
U.S. Appl. No. 15/519,835, filed Apr. 17, 2017, 2017/02039085, Miyashita et al.
Chinese Office Action dated Mar. 20, 2019, in Chinese Patent Application No. 201580039530.X, with English translation, 12 pages.
EPO Communication pursuant to Rules 70(2) and 70a (2) EPC dated Aug. 14, 2018, in European Patent Application No. 15853316.6, 11 pages.
EPO Communication pursuant to Article 94(3) EPC dated Nov. 28, 2019, in European Patent Application No. 15853316.6, 6 pages.
Gunasekara et al., "Polyols as phase change materials for low-grade excess heat storage", Energy Procedia vol. 61, 2014, pp. 664-669.
International Preliminary Report on Patentability received for PCT Application No. PCT/JP2015/079374, issued on Apr. 25, 2017, with English translation, 11 pages.
Hiroto Kidokoro, Method for Producing Heat Storage Elastomer Molding, 2010, p. 1-23.
Paraffin Wax (8002-74-2), Chemical Book, obtained Mar. 20, 2018, 4 pages.
U.S. Office Action dated Jan. 10, 2020, in U.S. Appl. No. 15/519,835, 24 pages.
U.S. Office Action dated Mar. 18, 2021, in U.S. Appl. No. 15/519,835, 10 pages.
U.S. Office Action dated Dec. 22, 2021, in U.S. Appl. No. 15/519,835, 12 pages.
U.S. Office Action dated May 6, 2022, in U.S. Appl. No. 15/519,835, 17 pages.
U.S. Office Action dated Apr. 25, 2023, in U.S. Appl. No. 15/519,835, 20 pages.
Tetsuhiko Yamaguchi, "Special Feature: Gels and Material Life", Material Life, vol. 12, No. 4, Oct. 2000, pp. 189-192, with partial English translation.

* cited by examiner

A

Beginning

B

50°C 2 weeks

C

50°C 4 weeks

D

50°C 6 weeks

A

B

C

D

A

B

C

D

TEMPERATURE CONTROL AGENT, AND HEAT-GENERATING COMPOSITION AND WARMING DEVICE EACH USING SAME

CROSS-REFERENCE TO RELATED APPLICATIONS

This application is a National Stage entry under § 371 of International Application No. PCT/JP2019/003587, filed on Feb. 1, 2019, and which claims the benefit of Japanese Application No. 2018-018047, filed on Feb. 5, 2018, the contents of both of which are hereby incorporated by reference in their entireties.

TECHNICAL FIELD

The present invention relates to a temperature control agent to be used for producing a warming device, which generates heat upon reaction with oxygen, such as a chemical body warmer or a hot pack structure, and a heat-generating composition and a packaging material each using the temperature control agent, and a warming device using any of them.

BACKGROUND ART

A warming device using a heat-generating composition that generates heat upon contact with oxygen or air is generally and widely used as medical instruments, such as a hot pack or a meridian stimulation warming tool, for relieving aches or pains by means of heat, or as daily necessities, such as a warming tool including a body warmer for cold weather.

The heat-generating composition to be used in such a warming device, most generally, comprises metallic powder such as iron powder, a salt such as a dietary salt, water, a water retention agent such as activated carbon, and the like as constituent components, and generates heat by oxidation heat generated upon reaction of the metal with oxygen. Therefore, conventionally, the inflow of oxygen has been controlled by air permeability, moisture permeability, the quality of materials, or the like of an air-permeable packaging material, particularly an air-permeable (porous) film, of a bag containing the heat-generating composition, in order to achieve a desired range of heat-generating properties according to the purpose of the warming device.

Among heat-generating properties, characteristics that can be controlled by such a method are maximum temperature, temperature rising time, duration, or the like of heat generation, and a product is designed to optimally exhibit these characteristics when the product is used under a certain condition. However, strict management of performance of the packaging material becomes a burden in terms of production costs. Moreover, even if a high-performance air-permeable packaging material is used, the performance originally planned may not be exhibited or a safety problem may occur in such a case where a designed ventilation volume is not achieved in the practical use due to use aspects, a pin hole of the bag, or the like.

For example, common disposable body warmers may vary in heat-generating temperatures due to the changes in the environmental temperature or the amount of air to be supplied to the body warmer, which changes are caused by indoor to or from outdoor movement, wearing or taking-off of a coat, or the like. Usage of such body warmers in bed is often prohibited. The reason for this is that heat dispersion is reduced when the body warmer is covered with a blanket or the like, and as a result of temperature increasing, there is a risk of low temperature burn injury. Further, disposable body warmers for use in shoes are planned to be used in an environment in which the inflow of air is limited, and thus the disposable body warmers for shoes are produced using packaging materials having relatively high air permeability. However, when the disposable body warmers for use in shoes are used in a practical manner, the amount of air to be supplied varies for each type of shoes so that a variation in temperature may occur or temperature may rapidly increase upon taking shoes off.

In addition, similar problems also arise in warming devices for medical use that require more accurate temperature control. For example, percutaneous absorption-type medical hot packs having a combination of a heating element and a medicine are known to have merits, such as an increase in effect and a decrease in medicine amount by increased efficiency of percutaneous absorption by heat. However, as described above, since stability in heat-generating temperature is not perfectly achieved by the conventional temperature control art, there is a problem in that temperature is not stable in practice so that the administered amount of the medicine is not stable. Further, although there is a need for a heating element for short-time use that uses no fire as a substitute for moxa cautery, such a heating element has not been widely used. This is because the moxa cautery uses heat of a high temperature zone, and it is risky to apply the disposable body warmer technique that lacks temperature stability.

Accordingly, the present inventors have found that the temperature stability of a warming device could be improved by mixing a particular temperature control agent in the heat generating composition or the packaging material of the bag comprising the composition (Patent Document 3).

In addition, while the warming device is composed of relatively stable components and can be stored for a certain period of time at a normal temperature by blocking oxygen, the maximum temperature thereof may decrease in case the device is exposed to temperature changes during strage, in particular to an environment under a high temperature. Such issues have not been considered.

CITATION LIST

Patent Documents

Patent Document 1: International Publication WO 1999/000078 A
Patent Document 2: Japanese Provisional Patent Publication JP 2001-170099 A
Patent Document 3: International Publication WO 2016/063815 A

SUMMARY OF THE INVENTION

Problem to be Solved by the Invention

An object of the invention is to provide a means for realizing simple temperature control (especially, control of the maximum heat-generating temperature) of a warming device in lower cost, the means that can be used instead of conventional temperature control or along with the same which controls an amount of supplied oxygen or air by an air-permeable film or the like, and the means for preventing or reducing lowering of the heat-generating temperature due to aging deterioration or storage under high temperatures of the warming device, and to provide a warming device using the same. In addition, another object of the invention is to provide a more accurate temperature control means that can be used for a warming device for medical use, and to provide a warming device for medical use that achieves further improvement in safety and effectiveness.

Means for Solving Problem

According to the invention, there are provided the following items:

[1] a temperature control agent for controlling maximum temperature of a warming device comprising a heat-generating composition that generates heat upon reaction with oxygen, wherein said temperature control agent comprises one or more aliphatic compounds that are in particulate form that will not pass through a 60-mesh standard sieve (standard size according to JIS Z8801-1: 250 μm), that have a melting point of 35° C. to 65° C. and that have a water solubility (g/100 mL) at 20° C. of 5 or less;

[2] the temperature control agent according to the item [1], wherein the aliphatic compound is in particulate form that will pass through a 16-mesh standard sieve (standard size according to JIS Z8801-1: 1,000 μm);

[3] the temperature control agent according to the item [1] or [2], wherein the temperature control agent comprises one or more compounds selected from the group consisting of a higher α-olefin polymer, paraffin wax, myristyl myristate, polyester polyol, and polyoxyethylene fatty acid diester;

[4] a heat-generating composition that generates heat upon reaction with oxygen comprising metallic powder, a salt, water, and activated carbon, wherein the heat-generating composition further comprises the temperature control agent according to any of the items [1] to [3];

[5] the heat-generating composition according to the item [3], wherein the heat-generating composition is in solid form;

[6] a warming device comprising a bag or container, wherein said bag or container contains the heat-generating composition according to the item [4] or [5], and has air permeability in at least a part thereof;

[7] the warming device according to the item [6], wherein at least the bag or container is contained in an airtight outer bag that substantially blocks oxygen;

[8] the warming device according to the item [6] or [7], for use as a disposable body warmer or a medical instrument; and

[9] the warming device according to the item [8], in which the medical instrument is a hot pack or a meridian stimulation warming tool.

Effect of the Invention

According to the invention, a simple, low-cost, and satisfactory temperature control means which can be used instead of, or in addition to, temperature control by an air-permeable film in a warming device is provided. Thus, a warming device having more excellent temperature stability and high safety and having stable maximum heat-generating temperature even after long-term storage can be realized. In particular, the invention provides a warming device that is suitable for being stored as long-term stockpile for emergency use and that has a reduced risk of low temperature burn injury, for example, even when the warming device is used while the user is sleeping. Specifically, for example, the invention provides the following items:

a warming device that has a reduced risk of low temperature burn injury caused by covering with a blanket and that can be safely used even while the user is in bed;

a disposable body warmer for use in shoes that can stably generate heat regardless of the type of shoes, does not cause rapid temperature increasing even when the shoes are taken off, and has high safety;

a percutaneous absorption-type medical hot pack that has a high level of temperature stability, and high safety and effectivity; and a warming device used as a meridian stimulation warming tool, such as moxa cautery, that can be safely used by controlling maximum temperature even in a high temperature zone.

MODE(S) FOR CARRYING OUT THE INVENTION

Temperature Control Agent

Figure 1:
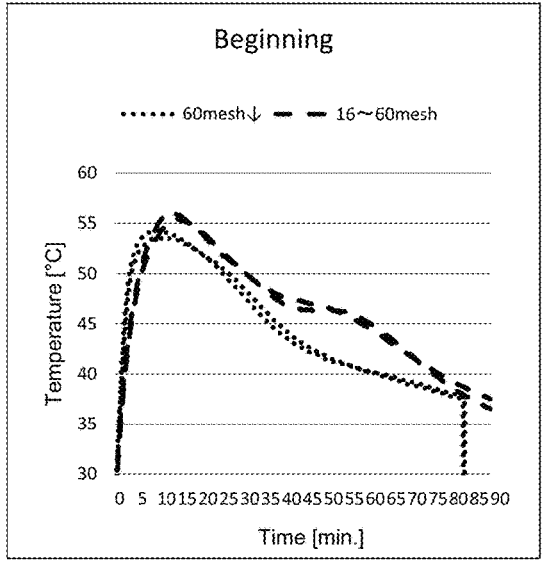
FIG. 1 is a diagram showing the results of a time-dependent deterioration test in which a warming device containing an α-olefin (having melting point of 58° C.) as the temperature control agent was stored at 50° C. "60 mesh₁" designates that a sample that passed through a 60-mesh standard sieve (standard size according to JIS Z8801-1: 250 μm) was used; and "16-60 mesh" designates that a sample that passed through a 16-mesh standard sieve (standard size according to JIS Z8801-1: 1,000 μm) and did not pass through a 60-mesh standard sieve (standard size according to JIS Z8801-1: 250 μm) was used. (The same applies to the following figures.) Panels (A), (B), (C), and (D) shows the heat generation patterns immediately after production, after storage for 2 weeks, after storage for 4 weeks, and after storage for six weeks, respectively.
Figure 1:
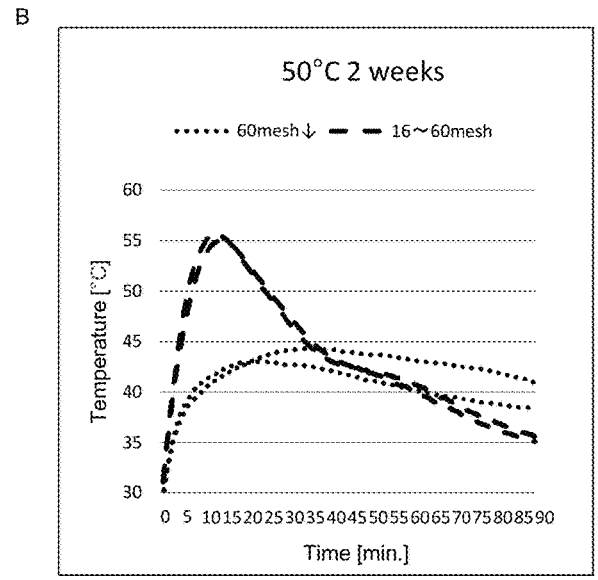
Figure 1:
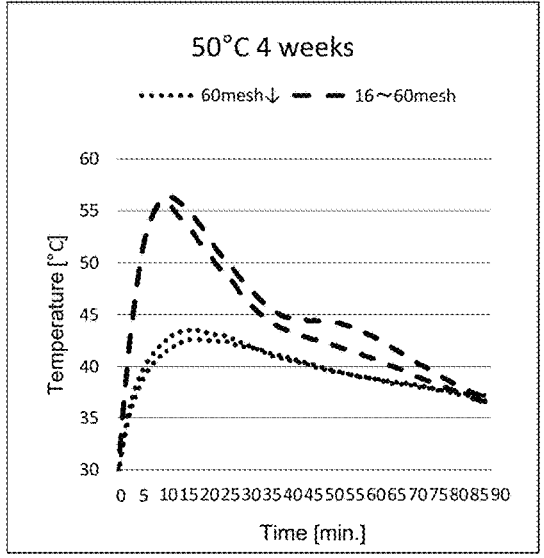
Figure 1:
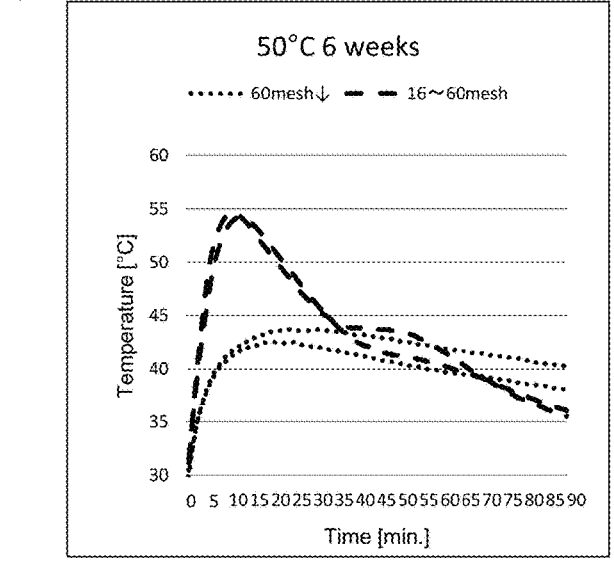
Figure 2:
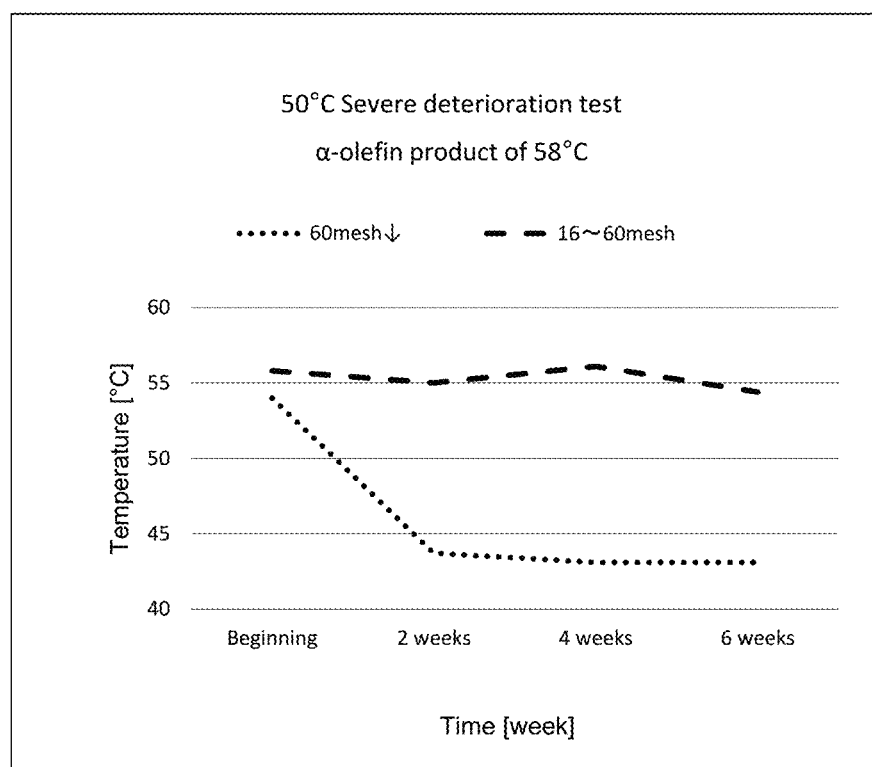
FIG. 2 is a diagram showing changes in the maximum temperature over time for the results shown in FIG. 1.
Figure 3:
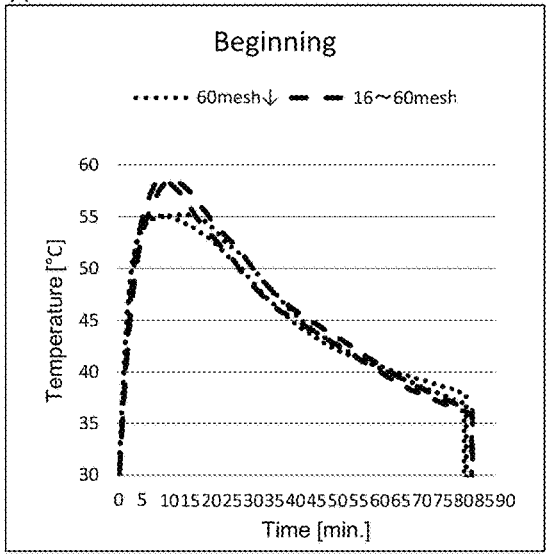
FIG. 3 is a diagram showing the results of a time-dependent deterioration test in which a warming device containing an α-olefin (having melting point of 62° C.) as the temperature control agent was stored at 50° C. Panels (A), (B), (C), and (D) shows the heat generation patterns immediately after production, after storage for 2 weeks, after storage for 4 weeks, and after storage for six weeks, respectively.
Figure 3:
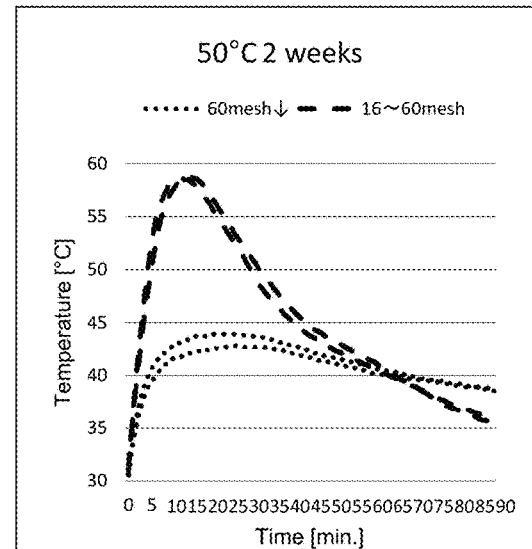
Figure 3:
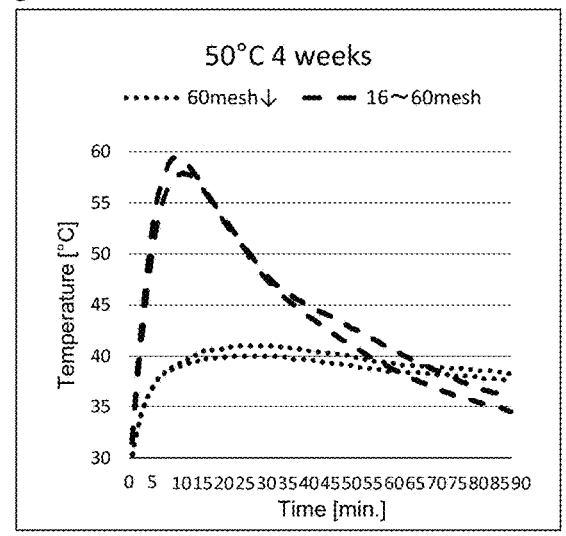
Figure 3:
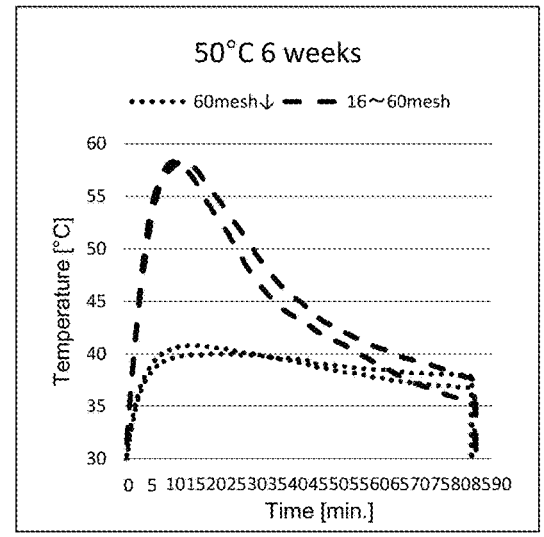
Figure 4:
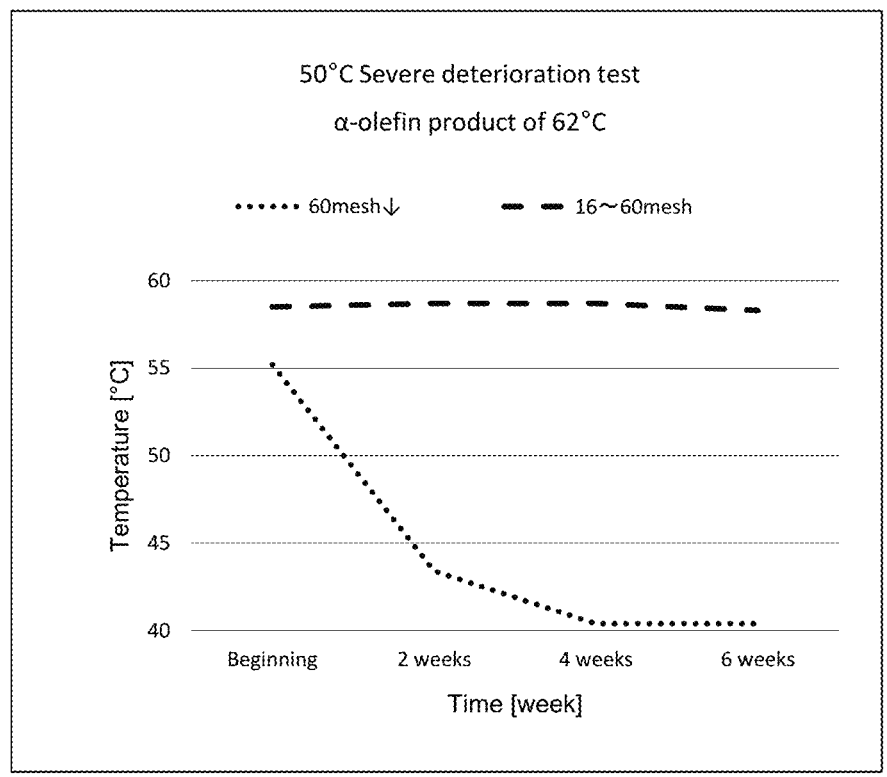
FIG. 4 is a diagram showing changes in the maximum temperature over time for the results shown in FIG. 3.
Figure 5:
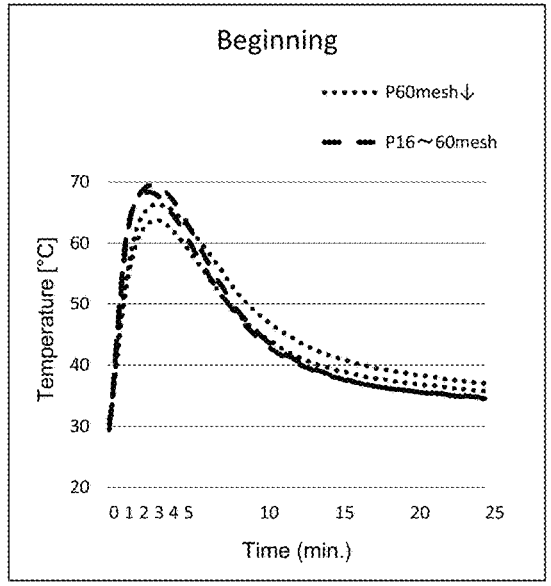
FIG. 5 is a diagram showing the results of a time-dependent deterioration test in which a warming device containing paraffin wax (P) as the temperature control agent was stored at 50° C. Panels (A), (B), (C), and (D) shows the heat generation patterns immediately after production, after storage for 2 weeks, after storage for 4 weeks, and after storage for six weeks, respectively.
Figure 5:
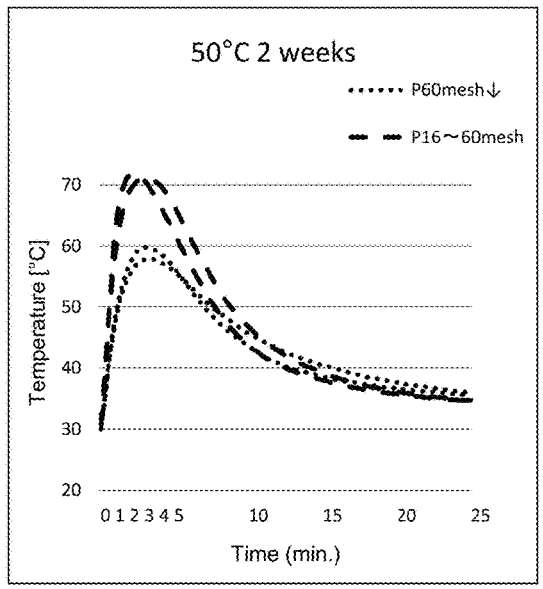
Figure 5:
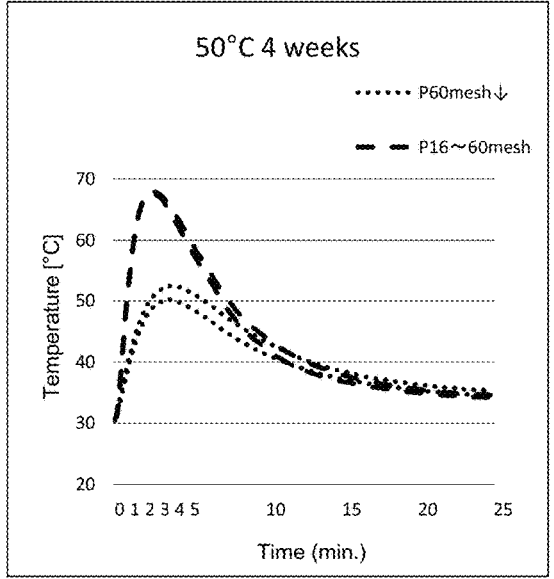
Figure 5:
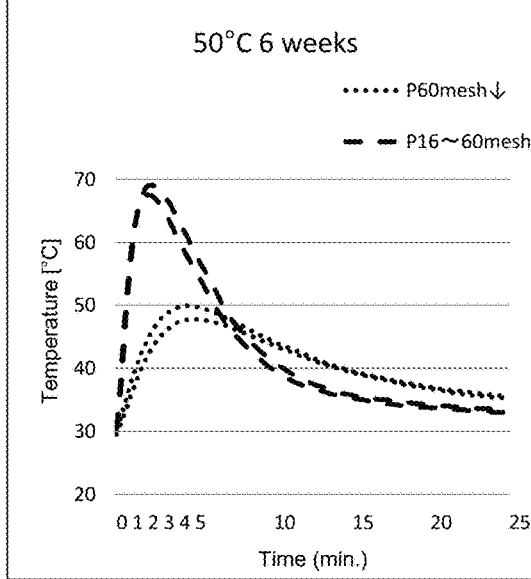
Figure 6:
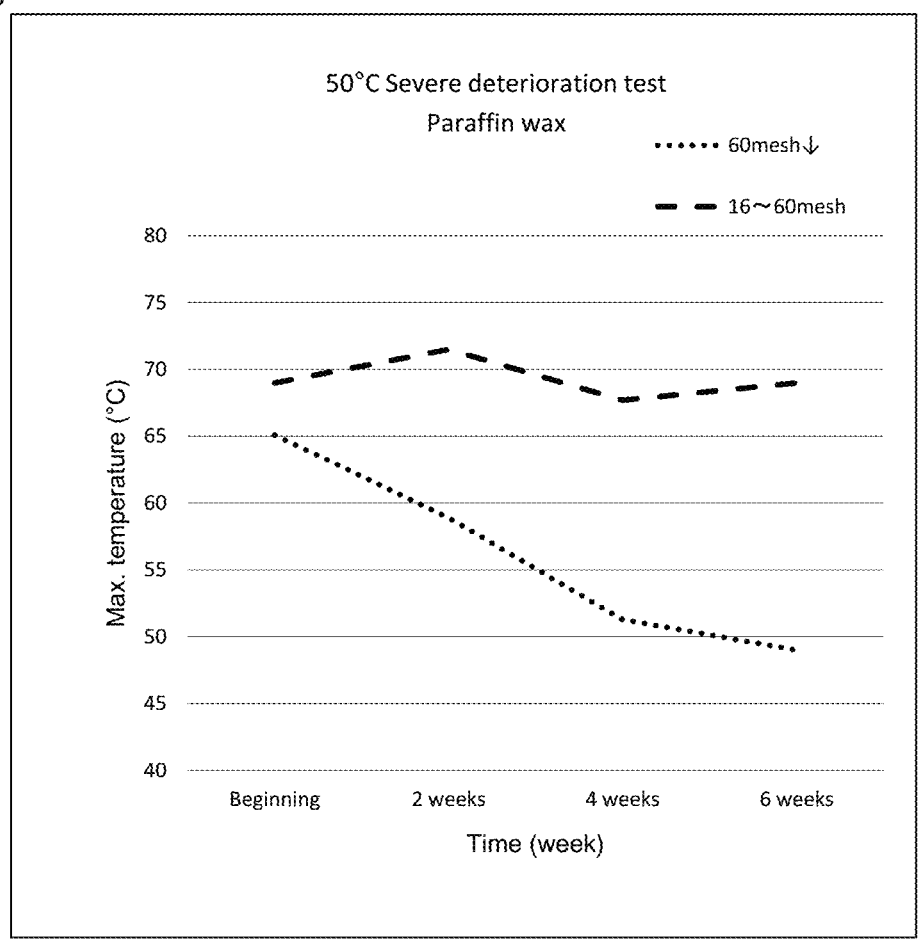
FIG. 6 is a diagram showing changes in the maximum temperature over time for the results shown in FIG. 5.

A temperature control agent of the invention is characterized by containing one or more aliphatic compounds that have a melting point of 35° C. to 65° C. and a water solubility (g/100 mL) at 20° C. of 5 or less. The solubility is preferably 3 or less and more preferably 1 or less. A preferable melting point varies depending on the usage of a warming device, but in general, it is preferably 38° C. to 60° C. As used herein, "an aliphatic compound" means, among those organic compounds, a compound in which all the carbon atms in a molecule are connected in a linear chain, or a compound in which the chain of carbon atoms has a branched structure but does not include a cyclic structure, including those having a cyclic structure containing oxygen or nitrogen that have a close relationship with the chain compound that is the parent thereof and that easily open the ring to become a chain compound, such as anhydrides of chain dicarboxylic acids, imides, lactones of oxyacids, and cyclic ethers.

An aliphatic compound having such properties can be selected from higher α-olefin polymers, various paraffin waxes such as those plant-derived, animal-derived, or petroleum-derived, myristyl myristate, polyester polyol, and polyoxyethylene fatty acid diester, and the like. In the present specification, a higher α-olefin polymer refers to a polymer obtained by copolymerization of two or more kinds of α-olefin having 10 to 35 carbon atoms or by copolymerization of one or more kinds of α-olefin having 10 to 35 carbon atoms with one or more kinds of other olefins. In other words, a higher α-olefin polymer refers to a copolymer of two or more α-olefins having 10 to 35 carbon atoms, or a copolymer of one or more α-olefins having 10 to 35 carbon atoms and one or more other olefins.

The higher α-olefin polymer to be used in the invention may be a main-chain crystallizable polyolefin whose main chain is fold to be crystalized, but it is preferably a side-chain crystallizable polyolefin having a certain long-chain α-olefin at the side chain. A side-chain crystallizable polyolefin has sharp melting behavior. When the side-chain crystallizable polyolefin is not melted, there is no stickiness, which is favorable. Such a side-chain crystallizable polyolefin is manufactured and sold, for example, as "HS Crysta" (Hokoku Corporation; product name) or the like, and is commercially available. Similarly, paraffin wax (for example, Nippon Seiro Co., Ltd.), myristyl myristate (for example, Croda Japan KK), polyester polyol (for example, DIC Corporation or Hokoku Corporation), polyoxyethylene fatty acid diester (for example, Sanyo Chemical Industries, Ltd.), and a higher α-olefin polymer are also commercially available.

The measurement of the melting point is performed using a differential scanning calorimeter as follows. To an aluminum (Al) container, 5 mg to 15 mg of a sample is input, and covered with a crimp cover made of Al, and then a certain pressure is applied to seal the container. The temperature is increased at a temperature increasing rate of 5° C./min from −50° C. of an estimated melting point to +30° C. of the estimated melting point while using the Al container+the clamp cover as a reference. After the temperature is held for 5 minutes, the temperature is decreased at the same rate and then held at −50° C. of the estimated melting point for 5 minutes. This operation is repeated twice, and the DSC curve at the second cycle (2nd-run) is measured. The melting point is read from the main endothermic peak appearing in the DSC curve by the endotherm associated with the melting of the sample.

The water solubility at 20° C. can be measured by dissolving a sample in 100 g (100 ml) of water at 20° C. and then reading the mass of the limit amount at which the sample is no longer dissolved (the maximum amount of the dissolved sample).

The aliphatic compound comprised in the temperature control agent of the invention can be present in the form of a pellet, powder, a block, or the like at normal temperature. The aliphatic compound in the form of a pellet, a block, or the like is used by subjecting it to pulverization (for example, freeze-pulverization) before use. After pulverization, the particle size is controlled to be within a predetermined range. The size of the particles of an aliphatic compound is herein indicated by sorting by means of standard sieves (Tyler sieves). The sizes of the openings of sieves are generally indicated by "mesh" or "μm" (the standard size (μm) of apertures of metal sieves under JIS Z8801-1 (2006), also called a nominal size), and the corresponding relationship is known. For the temperature control agent of the invention, commercially available aliphatic compound can be appropriately selected and used as is. It is also possible to appropriately select and formulate the compounds to obtain a desired heat-generating pattern by sieving (i.e., classifying) them using various standard sieves into particles that pass trough or that do not pass through the sieves. The aliphatic compound comprised in the temperature control agent of the invention needs to be in a particulate form that will not pass through the standard sieve of 60-mesh (aperture 250 μm). Further, the aliphatic compound desirably comprises those particles in a particulate form that will passes through the standard sieve of 16-mesh (aperture 1,000 μm).

As long as the particle size is within this range, the particles may have a completely uniform diameter, and there is no particular limitation on their distribution. Further, the shape of particles does not matter.

As used herein, "not passing through" a sieve having a certain aperture means that 60% or more, preferably 80% or more, and more preferably 90% or more, of particles as a whole do not or will not pass through the sieve. Most preferably, such particles amount 100%. Similarly, "passing through" a sieve having a certain aperture means that 60% or more, preferably 80% or more, and more preferably 90% or more, of particles as a whole pass or will pass through the sieve. Most preferably, such particles amount 100%.

The mechanism by which stability of the heat-generating properties is achieved by using the temperature control agent of the invention is not limited to a specific theory, but is basically considered as follows. In the case of adding the temperature control agent to a heat-generating composition, the temperature control agent is melted when the heat-generating temperature reaches a temperature near the melting point of the temperature control agent so that the periphery of iron powder is covered with the melted temperature control agent. Accordingly, oxidation reaction is inhibited, and thus temperature increasing is suppressed.

Further, when particles that do not pass through a 60-mesh standard sieve (aperture 250 μm) are used, compared to the case where particles with smaller sizes are used, it is considered that effects of temporary changes of environmental temperature during storage are reduced and that accidental melting (and declining of maximum heat-generating temperature) is difficult to occur. On the other hand, it is considered that particles that do not pass through a 16-mesh standard sieve (aperture 1,000 μm) take a long time to melt and the reaction stop tends to be delayed, and thus the maximum temperature becomes high. In particular, when used in a heat-generating composition in the form of tablet, etc., it is considered that the dispersed state of those particles tends to be uneven, and therefore the time to reach the maximum temperature tends to vary.

Incidentally, the maximum temperature and the heat generation pattern to be achieved vary depending on the usage of the warming device. Therefore, the type and the content of the temperature control agent are selected such that demanded heat generation performance is achieved.

For example, a hot pack or body warmer which is directly attached to the skin preferably generates heat at a heat generation temperature near 40° C., but it is said that at a temperature above 43° C., denaturation of protein may occur and thus the risk of low temperature burn injury increases. For this reason, the heat generation temperature of the hot pack or body warmer is designed not to exceed 43° C., and in a case where there is a possibility that the heat generation temperature becomes 43° C. or higher, it is desirable to rapidly suppress temperature increasing to near 40° C. which is a preferable heat generation temperature. On the other hand, a continuous decrease in temperature after such suppression is not desirable since the warming effect is decreased. Further, even in the case of a hot pack or body warmer which is directly attached to the skin, when it is to be attached to a woman's delicate abdominal part in order to alleviate menstrual cramps, mild heat generation of 40° C. or lower is preferable.

In the case of a disposable body warmer which is attached to clothes, it is used at a temperature near a maximum temperature of around 55° C. since the skin is protected by clothes. In the case of a disposable body warmer as a substitute for moxa cautery, which is used at a relatively high temperature and in a short time, it is desirable to design the disposable body warmer not to exceed a temperature near 55° C. since the disposable body warmer is in direct contact with the skin. Further, in the case of the substitute for moxa cautery, it is desirable to rapidly decrease temperature after the suppression of temperature increasing.

As described above, there are the maximum temperature and the heat generation pattern suitable for each of various warming devices. Therefore, in order to realize the temperature and pattern, it is possible to appropriately select, as the temperature control agent, one or more aliphatic compounds that have a melting point near a desired maximum temperature (for example, a melting point of about −20° C. to about +10° C. of the maximum temperature (that is, the maximum temperature is within about +20° C. to −10° C. of the melting point), preferably a melting point having a difference between the maximum temperature and the melting point within about ±8° C., and more preferably a melting point having a difference between the maximum temperature and the melting point within about ±5° C.), and to design the added amount thereof, addition method, addition of an arbitrary component, and the like. For example, in order to control the maximum temperature to about 55° C., α-olefin having a melting point of 58° C. can be selected.

Heat-Generating Composition

The heat-generating composition of the invention comprises at least metallic powder, a salt, water and activated carbon, and further comprises the temperature control agent of the invention. The temperature control agent is as described above.

As the metallic powder, iron powder is generally used, but any other metallic powder may be used as long as it generates oxidation heat. As a salt, inorganic salts such as sodium chloride, potassium chloride, and magnesium chloride are generally used. The heat-generating composition of the invention comprises activated carbon and may further comprise a water retention agent other than activated carbon (for example, a water absorptive polymer, vermiculite, sawdust, or a silica material). Further, as necessary, conventionally known various other components can be added.

Formulation examples of blending these components include, for example, when the weight of the heat-generating composition is regarded as 100%, a heat-generating composition comprising from 35 to 80% by weight of iron, 1 to 20% by weight of activated carbon, 1 to 10% by weight of salt, 5 to 45% by weight of water, and 0 to 45% by weight of water retention agent other than activated carbon. In the heat-generating composition of the invention, it is preferable that iron be contained in a range of 30 to 70% by weight, activated carbon be contained in a range of 1 to 15% by weight, a salt be contained in a range of 12 to 5% by weight, water be contained in a range of 20 to 30% by weight, a water retention agent other than activated carbon be contained in a range of 1 to 25% by weight, and a filler (excipient) be contained in a range of 5 to 30% by weight, preferably in a range of 10 to 30% by weight. The amount of the temperature control agent blended can be appropriately selected depending on the usage purpose of the warming device, the maximum temperature to be achieved, and the like as described above. For example, with respect of 100 parts by weight of the heat-generating composition having the above formulation, 3 to 40 parts by weight, preferably, 3 to 30 parts by weight of the temperature control agent of the invention is added and mixed.

A heat-generating composition can be produced by a known method by mixing indispensable components as described above and an arbitrary component(s) selected as necessary, under a low oxygen condition or an anoxic condition when a salt and water are added in advance. The heat-generating composition may be powder, which may be further processed by a known method. For example, it may be formed into embodiments, such as a cube shape by tableting, a sheet shape by rolling, or the like. In the case of forming the heat-generating composition in a solid form, a binder such as cellulose (for example, crystalline cellulose), lactose, starch, dextrin, sucrose ester, Teflon (registered trademark), polyethylene glycol, or carboxymethyl cellulose may be added. For example, in order to subject the heat-generating composition to tablet molding to form a tablet-type solid, 10 parts by weight or more, preferably, 10 to 30 parts by weight of a binder such as crystalline cellulose with respect to 100 parts by weight of the heat-generating composition is added so that a tablet having a desired and suitable hardness can be obtained. Such a solid-form heat-generating composition is favorable because it prevents a failure in sealing caused by attachment of powder to the sealing portion of a bag or container at the time of packing, and eliminates a variation in heat generation temperature. Incidentally, regarding the heat-generating composition, a salt may be added at the same time when powder raw materials are mixed or may be added as salt water.

The heat-generating composition of the invention containing the temperature control agent as described above can be tested as to whether a desired maximum temperature can be achieved, by measuring, according to the heat generation test of JIS S4100, changes in temperature over time when the heat-generating composition is reacted with oxygen in air via an air-permeable packaging material (for example, 17,000 to 18,000 sec/100 cc (JIS P8117 method (Gurley method)) used as a bag for containing the heat-generating composition. Incidentally, the heat generation test performed for this purpose may be performed while test conditions are appropriately modified such that an assumed situation of actual use is reflected.

Packaging Material

The heat-generating composition is charged in a bag for containing a heat-generating composition. The bag charged with the heat-generating composition can be used per se as a warming device (for example, a so-called non-stick-type body warmer) without any change. In general, the bag for containing a heat-generating composition is formed such that at least a part of the bag has air permeability.

The heat-generating properties of a heat-generating device (rising speed of heat generation, heat generation retention time, thermal conductivity to an object to be heated such as a human body or clothes, and the like) vary depending on the selection of the air-permeable packaging material configurating the bag for containing a heat-generating composition. Therefore, the air-permeable packaging material can be appropriately selected from known materials and used so that the heat-generating properties are in a desired range according to the usage purpose.

An air-permeable packaging material of 10,000 to 40,000 sec/100 cc (JIS P8117) is used in general body warmers such as those for a human body, and the like. Further, for example, an air-permeable packaging material of 2,000 to 7,000 sec/100 cc is used in a body warmer for use in shoes. Accordingly, as an air-permeable packaging material of a bag for containing a heat-generating composition, generally, a packaging material having an air permeability of 2,000 to 40,000 sec/100 cc is used. In the case of a warming device, which is designed to be used at high temperature and/or in a short time, such as a meridian stimulation warming tool, a packaging material of 0 to 10,000 sec/100 cc can be used. By using the temperature control agent of the invention, precise management for air permeability is not necessary depending on the usage of the warming device, and thus the acceptable range of usable air-permeable packaging materials is widened.

As an air-permeable packaging material used for the bag in the invention, a film or sheet entirely or partially having air permeability may be used. In general, as an air-permeable packaging material, a single-layered or laminated porous film or sheet may be used alone or in combination with a woven fabric or non-woven fabric, etc. Alternatively, a single-layered or laminated non-porous film or sheet, alone or in combination with a woven fabric or non-woven fabric etc., may be provided with needle holes and used. Incidentally, as used in the invention, a "film" mainly indicates a single product (including a single-layered or laminated product; the same applies in the following) or a relatively thin product, and a "sheet" mainly indicates a single product, a laminate of two or more single products, or a relatively thick product; however, they are not strictly distinguished.

As a resin constituting a film, generally, a thermoplastic synthetic resin or the like is used. Specifically, polyethylene, polypropylene, polyester, polyamide, polyvinyl alcohol, polyvinyl chloride, polyvinylidene chloride, polyurethane, polystyrene, an ethylene-vinyl acetate copolymer, polycarbonate, or the like is preferably used either alone or in combination. Depending on the purpose, a resin can be appropriately selected according to appropriate necessary heat generation amount, temperature, a heat-generating composition to be used, or the like.

In the invention, as an air-permeable film or sheet, a stretched film, preferably, a stretched porous film or a sheet comprising the same is suitably used. The stretched porous film generally contains an inorganic filler and has communication holes formed by stretching so that air permeability is exhibited, and the air permeability can be controlled by controlling this hole diameter or the like.

In the case of performing lamination, generally, it is performed by a laminating method but is not limited thereto. Any conventionally known method can be employed in lamination. For example, lamination may be performed by a method using thermal bonding, or by means of an adhesive such as a hot-melt adhesive or an acrylic or urethane adhesive. The surfaces may be completely bonded, or may be partially bonded in order to maintain flexibility. A curtain spray method or dry lamination method is preferably used.

A non-woven fabric is used in the air-permeable packaging material from the viewpoint of reinforcing the packaging material strength, improving mechanical adequacy, and the like. As a non-woven fabric which may be laminated with the above-described film, a product conventionally used in the technical field of a heating element, a medical heating tool, or the like is suitably used. Examples of the non-woven fabric include non-woven fabrics comprising synthetic fibers such as nylon, vinylon, polyester, rayon, acetate, acrylic, polyethylene, polypropylene, and polyvinyl chloride; and non-woven fabrics comprising natural fibers such as cotton, hemp, and silk. Non-woven fabrics in the form of spunbond, thermal bond, spunlace, or the like are mentioned. The weight of the non-woven fabric varies depending on the specific weight of the non-woven fabric material or the bulk height by a difference in interlacing method, but generally, the weight is suitably about 10 $g/m^2$ to about 200 $g/m^2$ and particularly preferably about 20 $g/m^2$ to about 100 $g/m^2$.

In particular, an air permeable sheet which is obtained by laminating a non-woven fabric of nylon fibers, polyester fibers, or the like with a stretched porous film of a thermoplastic synthetic resin is generally and widely used.

A part of the bag, for example, a packaging material at a rear side of a flat bag may be an air-permeable packaging material as described above or may be an air-impermeable packaging material. The air-impermeable packaging material can be formed in a single layer or a laminated film or sheet of a resin as described above, and there is no particular limitation on the material, thickness, configuration, and the like as long as the air-impermeable packaging material is suitable for the production of the bag for containing a heat-generating composition.

The bag for containing a heat-generating composition can be produced using the packaging material as described above by attaching periphery portions to each other by a method generally used in the technical field. The warming device can be basically produced by packing the heat-generating composition of the invention in the bag. In general, the production of the bag and the production of the heat-generating device are continued. First, the periphery portions of the layered packaging materials are adhered to each other by heat sealing or an adhesive while a part of the periphery portions is left open. The heat-generating composition is dispensed into the bag from the opening portion, and then the opening portion is also adhered to contain the heat-generating composition.

Further, in case of a product having a small application area and/or a short use time such as a moxibustion tool, the heat-generating composition may be contained, for example, in a container having a thickness of about several mm to several cm, instead of the flat bag, and used. Also, in this case, packaging materials of various properties as described above can be appropriately used in production of a lid (a top member) and a container body. For example, the top member can arbitrary comprise a layer or layers such as a sealant material (3a), non-woven fabric (3b), adhesive (3c), release paper (3d) and the like as needed. As a specific example, it can be LLDPE (30 μm)/PET spunlase non-woven fabric (30 g/m$^2$)/SIS-type hotmelt adhesive/PET separator (38 μm), in order from 3a. Incidentally, as described above, in the case of a product using high-temperature and/or short-time heat generation such as a moxibustion tool, a packaging material having extremely high air permeability can be used and thus a non-woven fabric may be used alone as the top member and/or the container body.

Warming Device

The warming device can be configured by only a bag (for example, a non-stick-type disposable body warmer) or a container (for example, a moxibustion tool) that is charged with the heat-generating composition of the invention as described above. It can further comprise additional elements as necessary. These various elements are known and may be integrated with the bag or may be provided as a separate member to be assembled at the time of use. As examples of the additional elements, there are mentioned various means for fixing the bag or container and various parts to be assembled with the bag or container at the time of use (for example, parts to be used according to the usage of the warming device, such as a container containing a perfume or a medicine and a sheet containing water or a cosmetic material). As the fixing means, for example, there are mentioned an adhesive layer or wet pack layer, which is formed on the surface of a part of the bag or container for containing a heat-generating composition, enabling the warming device to be pasted to an object to be heated, a band-shaped member used for fixation by winding the member on an object to be heated, and a mask, supporter, or wrist band, which is provided with a pocket for containing a heat-generating device, and the like. Further, for the purpose of temperature adjustment or the like, a seat may be provided between a container and an adhesive layer so as to adjust a distance and/or space between an application part and the warming device. Incidentally, regarding the warming device of the invention, various agents such as camphor and menthol, or a perfume may be used in combination with a constituent element such as an adhesive layer or a wet pack layer, or a heat-generating composition, and/or a packaging material or a container. For example, as a heat-sensing receptor, *capsicum* tincture, *capsicum* extract, powdered *capsicum*, ginger tincture, ginger extract, powdered ginger, fennel tincture, fennel extract, powdered fennel, capsaicin, capsaicin derivative, vanillyl butyl ether, vanillyl alkyl ether, nonylic acid vanillylamide, or the like can be added to the adhesive. As a cold-sensing receptor, 1-menthol, *Mentha arvensis*, dl-camphor, peppermint oil, thymol, menthyl ethylamido oxalate, or the like can be added to the adhesive.

Of the warming device, at least the bag or container that contains the heat-generating composition is enclosed in an outer bag that blocks oxygen, and then stored until the use thereof. Such an outer bag is also known. As the outer bag for long-term storage, those having a low oxygen permeability in order for suppressing oxidation reaction of ferros during storage, or comprising a layer of aluminum with a low vapor permeability in order for suppress release of vapor from the outer bag are particularly preferable.

EXAMPLES

<Production of Moxibustion Tool>

Figure 7:
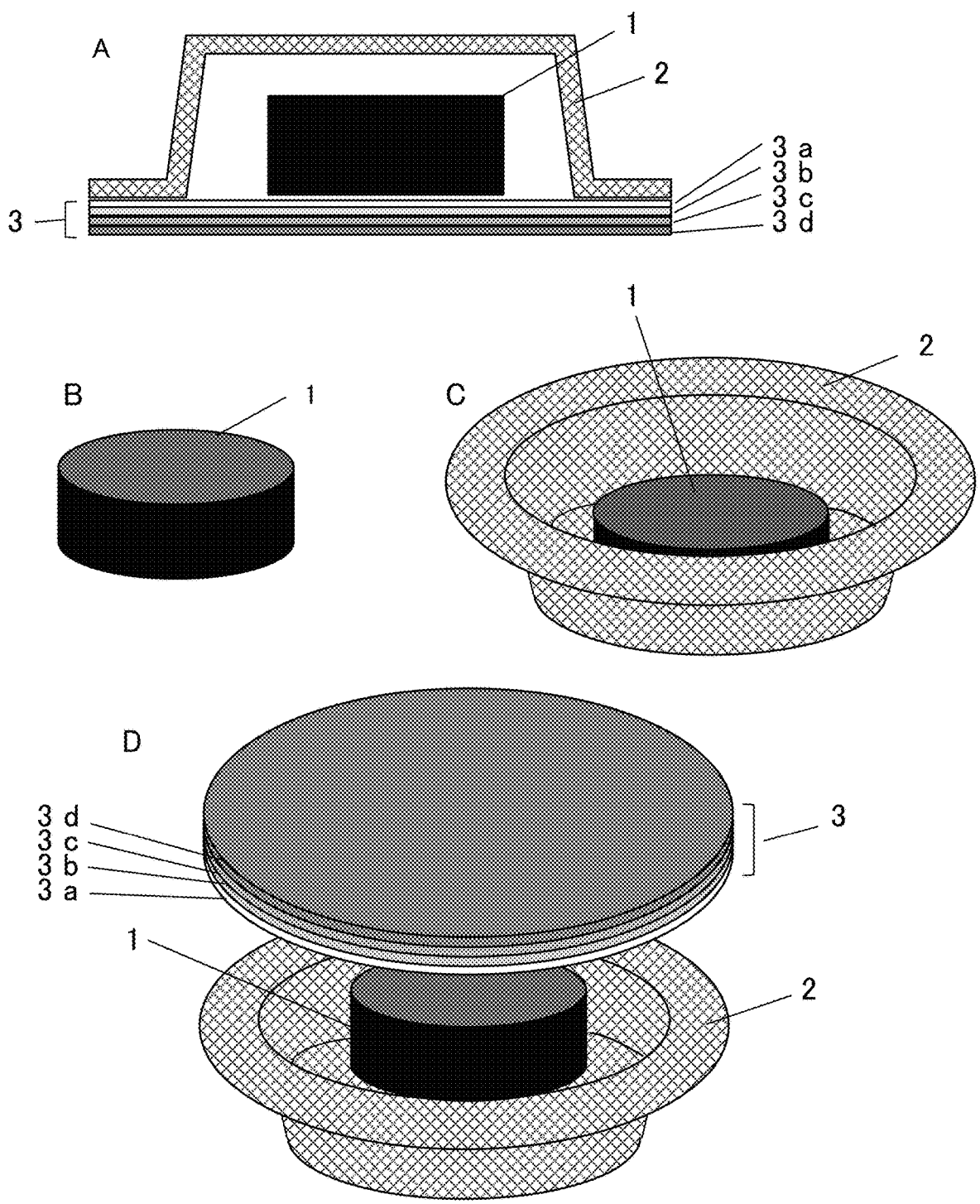
FIG. 7 is a diagram illustrating an example of the structure of a meridian stimulation warming tool (a moxibustion tool) of the invention. Panel A is a cross-sectional view of the moxibustion tool, Panel B is a perspective view of a heat-generating composition tablet (1), Panel C is a perspective view of a state of a container body (2) in which a heat-generating composition tablet (1) is placed, and Panel D is a perspective view illustrating the container body (2) having the heat-generating composition tablet (1) input therein along with a top member processed to have an adhesive layer (an adhesive tape) (3) that is to be appended to the container body. It is noted that the heat-generating composition tablet (1) in FIG. 7 is schematically illustrated in the form before water (or salt water) is added (before swelling).

A moxibustion tool similar to the one as shown in FIG. 7 consisting of a container body (2) in which a heat-generating composition tablet (1) is placed and a top member (3) was produced as follows. As the raw materials of the heat-generating composition, iron powder (Powdertech Co., Ltd., reduced iron powder "RDH-3M"), activated carbon (Osaka Gas Chemicals Co., Ltd., wood flour-based activated carbon "Shirasagi S5"), a water absorptive polymer (Sanyo Chemical Industries, Ltd., polyacrilic acid-type resin "ST-500D"), crystalline cellulose (Asahikasei Chemicals, Co., Ltd., crystalline cellulose "Ceolus TG-101"), a salt (Nihonkaisui Co., Ltd., powder salt "EF-300"), and aliphatic compound(s) as explained below (α-olefin: Hokoku Corporation, "HS Crysta 6100"; paraffin wax: NIPPON SEIRO CO., LTD., "SP-0145") were used. The composition of the heat-generating composition was 45 parts of iron powder, 3.5 parts of activated carbon, 5 parts of water absorbtive polymer, 20 parts of crystalline cellrose, 3.5 parts of salt, and 25 parts of aliphatic compound(s) as the temperature control agent ("part(s)" is always "part(s) by weight").

Pulverization and sieving of the aliphatic compounds were performed as follows. Each of the aliphatic compounds, melted at 100° C. in a low temperature dryer by Isuzu Manufacturing Co., Ltd., was flown on a PET film to form a plate-like shape having a thickness of about 2 mm and allowed to cool at room temperature. The fully solidified plate was coarsely pulverized by hand to pieces of about 10 mm square. This coarsely pulverized product was pulverized with a stainless steel coffee mill (sold by Yunox Cooperation, catalog number HG6063).

The pulverized product was manually sieved by a JIS standard stainless steel sieve (Tokyo Screen Co. Ltd., frame size, diameter 200×60 mm, JIS Z8801-1:2000 specification) to obtain a sample of a temperature control agent.

First, in consideration of the bulk specific weight and particle diameter, the cellulose, the aliphatic compound, the water-absorbing polymer, the activated carbon, the salt, and the iron were sequentially weighed and added into a beaker in this order. The add materials were stirred evenly with a medicine spoon so as to eliminate uneven distribution of each raw material. Two g of this mixture of raw materials was weighed and tableted using "Desktop Prototype Tableting Machine QUICK MINI FY-TQM-30" by Fuji Yakuhin Kikai Co. Ltd. (tabletting pressure, 15 KN). A cylindrical tablet having a diameter of 17 mm and a thickness of 7 mm was produced by using the pressing mold having a diameter of 16.9 mm and the receiving mold having an inner diameter of 17 mm.

The container for containing the heat-generating composition tablet was manufactured as follows. First, a prototype mold made of wood (upper: a cylindrical rod, lower: a receiving wood mold having a hole formed therein) was prepared, and the pressing surface of the cylindrical rod was heated to 200° C. using a laboratory hot stirrer or hot plate. A moldable non-woven fabric (Asahi Kasei Corp., heat moldable non-woven fabric, Smash "Y15200 200 g/m$^2$") placed on the receiving wood mold was pressed with the heated rod to thereby produce a cup-shaped molded product.

The tablet was placed in the molded non-woven fabric container body, and a top member (OPP 20 μm/LLDPE 30 μm; Toho Packaging Inc.) was adhered to the top of the container with a household iron. Using a syringe, 0.8 g of water was added to the 2 g of tablet from the top member.

The resulting product was sealed in an airtight outer bag (PET 12 μm/aluminum foil 7 μm/LLDPE 50 μm, Toho Packaging Inc.).

When paraffin wax was used, the pressing mold having a diameter of 13.9 mm and the receiving mold having an inner diameter of 14 mm were used to produce a cylindrical tablet having a diameter of 14 mm and a thickness of 4 mm (a tablet of 1 g), and 0.3 g of water was added to the 1 g of tablet.

<Measurement of Melting Point and Solubility>

The melting point of each aliphatic compound was measured by using a differential scanning calorimeter. As a measurement apparatus, a differential scanning calorimeter (DSC6220) connected to a fully automatic cooling unit and an analysis system (EXSTAR 6000 thermoanalytical rheology system, software: DSC Muse measurement software and DSC Muse standard analysis software) (all manufactured by Seiko Instruments Inc.) was used, and as a sample container, an open-type sample container made of Al (φ5.2 H2.5 (50 μl)) and an open-type sample container made of Al (a crimp cover) were used.

To the Al container, 5 mg to 15 mg of a sample was input, the crimp cover made of Al was placed thereon, and then a certain pressure was applied to seal the container. The temperature was increased at a temperature increasing rate of 5° C./min from −50° C. of an estimated melting point to +30° C. of the estimated melting point while using the Al container+the clamp cover as a reference. After the temperature was held for 5 minutes, the temperature was decreased at the same rate and then was held at −50° C. of the estimated melting point for 5 minutes. This operation was repeated twice, and the DSC curve at the second cycle (2nd-run) was measured. The melting point was determined as described above from the endothermic peak appearing in the DSC curve by the endotherm associated with the melting of the sample.

The solubility to water was measured by dissolving powder of each aliphatic compound in 100 g (100 ml) of water at 20° C. and then reading the mass of the limit amount at which the sample was not dissolved.

The melting point was 57° C. for α-olefin (melting point 58° C.), 59.5° C. for α-olefin (melting point 62° C.), and 62.3° C. for paraffin wax. Solbility was less than 1 g/100 ml for all substances.

Storage tests were performed using Advantec Toyo Kaisya, Ltd., low temperature constant temperature constant humidity chamber THE051FA, under the conditions of 50° C. and 35% humidity. Storage for two weeks at 50° C. is equivalent to storage for one year at normal temperature. Similarly, it is considered that storage for four weeks and six weeks at 50° C. is equivalent to storage for two years and three years at normal temperature, respectively. The temperature setting of 50° C. was adopted in consideration of the conversion to room temperature on the Arrhenius plot, the storage at the warehouse, and the container transportation by sea.

<Heat Generation Test of Moxibustion Tool>

A heat generation test was performed according to the method of JIS S4100 "Disposable warmer" under conditions including an ambient temperature of 20±1° C., a wind speed of 0.5 m/s or less (dead calm), an ambient humidity of 55 to 70%, and 30±1° C. of the warming portion of a warming apparatus comprising a heater and a water circulating thermostatic bath. Since the moxibustion tool is attached directly onto the skin at the time of use, measurement was performed by pasting the moxibustion tool directly onto the surface of the heater.

The heat generation test was performed in such a manner that 8 L/min of hot water was circulated in a tank-shaped heater with a size of W 615×D 410×H 60 mm (using a vinyl chloride plate having a thickness of 8 mm) equipped with a water-circulating thermostatic bath and installed in a constant temperature room (room temperature: 20° C., humidity: 65%) to control the surface temperature of the heater (the vinyl chloride plate) to 30° C., and a moxibustion tool sample was pasted onto the vinyl chloride plate of the heater surface with the container body faced downward, and a temperature measurement sensor pasted around the center of the bottom surface of the container body with a double-sided tape (temperature measurement machine: Chino Corporation, Graphic recorder KR2S00; sensor: Anritsu Meter Co., Ltd., "ST-22E-005").

The results are presented in FIGS. 1 to 6.

From the above results, it is demonstrated that the warming device using the heat-generating composition that contains the temperature control agent of the invention was hardly affected by long-term strage with respect to the maximum heat generation temperature. Therefore, the warming device using the heat-generating composition that contains the temperature control agent of the invention has high levels of temperature stability and safety, and can maintain the heat generation performance as designed for a long period of time.

This application is based on the Japanese Patent Application No. 2018-018047 filed on Feb. 5, 2018, and the entire disclosure of the specification and claims of the Japanese Patent Application No. 2018-018047 is incorporated herein.

EXPLANATIONS OF LETTERS OR NUMERALS

1 HEAT-GENERATING COMPOSITION
2 CONTAINER (BODY)
3 TOP MEMBER
3a SEALANT MATERIAL
3b NON-WOVEN FABRIC
3c ADHESIVE
3d RELEASE PAPER

The invention claimed is:

1. A temperature control agent for controlling maximum temperature of a warming device comprising a heat-generating composition that generates heat upon reaction with oxygen, wherein said temperature control agent comprises:
   one or more aliphatic compounds that are in particulate form, that do not pass through a 60-mesh standard size sieve according to JIS Z8801-1: 250 μm, that have a melting point of 35° C. to 65° C., and that have a water solubility at 20° C. of 5 g/100 mL or less,
   wherein the one or more aliphatic compounds are in particulate form that passes through a 16-mesh standard size sieve according to JIS 28801-1: 1,000 μm, and
   wherein the temperature control agent comprises the one or more aliphatic compounds selected from the group consisting of a higher α-olefin polymer, paraffin wax, myristyl myristate, polyester polyol, and polyoxyethylene fatty acid diester.

2. A heat-generating composition that generates heat upon reaction with oxygen, comprising:
   metallic powder,
   a salt,
   water,
   activated carbon, and
   the temperature control agent according to claim 1.

3. The heat-generating composition according to claim 2, wherein the heat-generating composition is in solid form.

4. A warming device, comprising:
a bag or container,
wherein said bag or container comprises the heat-generating composition according to claim 2, and has air permeability in at least a part thereof.

5. The warming device according to claim 4, wherein at least the bag or container is contained in an airtight outer bag that substantially blocks oxygen.

6. The warming device according to claim 4, wherein the warming device is configured as a disposable body warmer or a medical instrument.

7. The warming device according to claim 6, wherein the medical instrument is a hot pack or a meridian stimulation warming tool.

8. The heat-generating composition according to claim 2, further comprising a binder.

9. The heat-generating composition according to claim 8, which is in the form of a tablet.

10. The heat-generating composition according to claim 2, wherein the heat-generating composition is a solid or formed composition.

11. The heat-generating composition according to claim 10, wherein the solid or formed composition is formed by tableting or rolling.

12. The heat-generating composition according to claim 2, wherein the temperature controlling agent comprises the higher a-olefin polymer.

13. The heat-generating composition according to claim 2, wherein the temperature controlling agent comprises the paraffin wax.

14. The temperature control agent according to claim 1, wherein the aliphatic compounds that are in particulate form consists of particles having a particle size of from 250 to 1000 microns.

15. The temperature control agent according to claim 1, wherein the temperature controlling agent comprises the higher a-olefin polymer.

16. The temperature control agent according to claim 1, wherein the temperature controlling agent comprises the paraffin wax.

* * * * *